United States Patent
Blanchard et al.

(10) Patent No.: US 11,224,651 B2
(45) Date of Patent: Jan. 18, 2022

(54) COMPOSITIONS COMPRISING HUMAN MILK OLIGOSACCHARIDES FOR USE IN INFANTS OR YOUNG CHILDREN TO PREVENT OR TREAT ALLERGIES

(71) Applicant: NESTEC S.A., Vevey (CH)

(72) Inventors: Carine Blanchard, Le Mont-sur-Lausanne (CH); Chiara Nembrini, Oron-la-Ville (CH)

(73) Assignee: Societe des Produits Nestle S.A., Vevey (CH)

( * ) Notice: Subject to any disclaimer, the term of this patent is extended or adjusted under 35 U.S.C. 154(b) by 0 days.

(21) Appl. No.: 16/071,597

(22) PCT Filed: Jan. 26, 2017

(86) PCT No.: PCT/EP2017/051580
§ 371 (c)(1),
(2) Date: Jul. 20, 2018

(87) PCT Pub. No.: WO2017/129640
PCT Pub. Date: Aug. 3, 2017

(65) Prior Publication Data
US 2019/0054165 A1 Feb. 21, 2019

(30) Foreign Application Priority Data

Jan. 26, 2016 (EP) ..................................... 16152753

(51) Int. Cl.
*A61K 39/35* (2006.01)
*A23L 33/00* (2016.01)
*A61P 37/08* (2006.01)

(52) U.S. Cl.
CPC .............. *A61K 39/35* (2013.01); *A23L 33/40* (2016.08); *A61P 37/08* (2018.01); *A23V 2002/00* (2013.01)

(58) Field of Classification Search
CPC ........ A61K 31/702; A61K 31/70; A61K 39/35
See application file for complete search history.

(56) References Cited

U.S. PATENT DOCUMENTS

| | | | |
|---|---|---|---|
| 2011/0064707 A1* | 3/2011 | Rochat | A61K 31/702 424/93.45 |
| 2012/0171165 A1* | 7/2012 | Buck | A61K 31/702 514/23 |
| 2012/0171166 A1 | 7/2012 | Chow et al. | |
| 2014/0249103 A1 | 9/2014 | Buck et al. | |

FOREIGN PATENT DOCUMENTS

| | | |
|---|---|---|
| EP | 2454948 | 5/2012 |
| EP | 2455387 | 5/2012 |
| EP | 2465508 | 6/2012 |
| EP | 2522232 A1 | 11/2012 |
| WO | WO 2012/069415 A1 * | 5/2012 ............... C07H 3/06 |
| WO | 2015071131 | 5/2015 |
| WO | 2015071403 | 5/2015 |
| WO | 2016046294 | 3/2016 |

OTHER PUBLICATIONS

Asakuma (European Journal of Clinical Nutrition; 2008, 62, 488-494).*
Renz-Polster (Clinical and Experimental Allergy, 35: 1466-1472; 2005).*
Yang et al., "In vitro characterization of the impact of selected dietary fibers on fecal microbiota composition and short chain fatty acid production" Anaerobe, 2013, vol. 23, pp. 74-81.
Gibson et al., "Dietary Modulation of the Human Colonic Microbiota: Introducing the Concept of Prebiotics" J. Nutr. 1995, vol. 125, pp. 1401-1412.
Lodge et al. "Breastfeeding and asthma and allergies: a systematic review and meta-analysis" Acta Paediatrica, 2015, vol. 104, pp. 38-53.
Ostblom et al. "The impact of food hypersensitivity reported in 9-year-old children by their parents on health-related quality of life" Allergy, 2008, vol. 63, pp. 211-218.
Salminen et al. "Probiotics: how should they be defined?" Trends in Food Science & Technology, 1999, vol. 10, pp. 107-110.
Stark et al. "In Vitro Production of Short-Chain Fatty Acids by Bacterial Fermentation of Dietary Fiber Compared with Effects of Those Fibers on Hepatic Sterol Synthesis in Rats" J. Nutr., 1993, vol. 123, pp. 2166-2173.
Trompette et al. "Gut microbiota metabolism of dietary fiber influences allergic airway disease and hematopoiesis" Nature Medicine, Feb. 2014, vol. 20, No. 2, pp. 159-166.
Wrodnigg et al. "The Heyns Rearrangement Revisited: An Exceptionally Simple Two-Step Chemical Synthesis of D-Lactosamine from Lactulose" Angew. Chem. Int. Ed., 1999, vol. 38, No. 6, pp. 827-828.
Kobata "Structures and application of oligosaccharides in human milk" Proc. Jpn. Acad., Scr. B, 2010, vol. 86, pp. 731-747, XP002612998.
EFSA Panel on Dietetic Products, Nutrition and Allergies (NDA) Scientific Opinion Entitled "Statement on the safety of Tacto-N-neotetraose and 2'-O-fucosyllactose as novel food ingredients in food supplements for children" EFSA Journal, 2015, vol. 13, No. 11, 11 pages.
Li et al. "Microbial Composition and In Vitro Fermentation Patterns of Human Milk Oligosaccharides and Prebiotics Differ between Formula-Fed and Sow-Reared Piglets" J. Nutr., 2012, vol. 142, pp. 681-689.

(Continued)

*Primary Examiner* — Pancham Bakshi
(74) *Attorney, Agent, or Firm* — K&L Gates LLP

(57) ABSTRACT

The present invention relates to a nutritional composition comprising at least one fucosylated oligosaccharide and at least one N-acetylated oligosaccharide, for use in preventing and/or treating allergy symptoms in an infant or a young child, by increasing propionate production, in said infant or young children.

13 Claims, 3 Drawing Sheets

(56) References Cited

OTHER PUBLICATIONS

Bode, "Human Milk Oligosaccharides: Every Baby Needs a Sugar Mama", Glycobiology, vol. 22, Issue No. 9, Apr. 18, 2012, pp. 1147-1162, XP55199362.
European Communication pursuant to Article 94(3) EPC dated Aug. 23, 2019 mailed in corresponding European Patent Application No. 17 702 062.5-1105, 7 Pages.
Tao et al., "Bovine Milk Glycome", Journal of Dairy Science, vol. 91, Issue No. 10, 2008, pp. 3768-3778.
Urashima et al., "Recent Advances in Studies on Milk Oligosaccharides of Cows and Other Domestic Farm Animals", Bioscience Biotechnology and Biochemistry, vol. 77, issue No. 3, 2013, pp. 455-466.
Munoz et al., "2'-Fucosyllactose: An Abundant, Genetically Determined Soluble Glycan Present in Human Milk", Nutrition Reviews, vol. 71, Issue No. 12, 2013, pp. 773-789.

\* cited by examiner

COMPOSITIONS COMPRISING HUMAN MILK OLIGOSACCHARIDES FOR USE IN INFANTS OR YOUNG CHILDREN TO PREVENT OR TREAT ALLERGIES

CROSS REFERENCE TO RELATED APPLICATIONS

The present application is a National Stage of International Application No. PCT/EP2017/051580, filed on Jan. 26, 2017, which claims priority to European Patent Application No. 16152753.6, filed on Jan. 26, 2016, the entire contents of which are being incorporated herein by reference.

FIELD OF THE INVENTION

This invention relates to nutritional compositions comprising specific oligosaccharides for use in preventing and/or treating allergies in infants or young children by increasing propionate, in particular colonic propionate, production in such infants or young children. The nutritional compositions of the invention are aimed at allergy prevention and allergy treatment. In the first case, infants or young children are healthy, with a normal risk of developing allergy or with a higher risk of developing allergy because one first degree family member have or have had allergy. In the second case, infants or young children are allergic or in needs, hence sick.

BACKGROUND OF THE INVENTION

Allergies are among the most common health problems affecting the life of patients of all age. Allergic diseases are nowadays recognized as an epidemic by the World Health Organization. The prevalence of allergies has been shown to increase in the past decades. Modern life style, especially urban, has been associated with high prevalence and higher severity of allergic manifestations.

Allergic sensitization in childhood, especially in early childhood and especially to food allergens, is critical and of highest interest as development of an "allergic phenotype" or "atopy" has been shown to facilitate subsequent sensitization and allergic reactions to other allergens. Hence allergies in childhood can be the first step of an allergic cascade leading to multiple allergies later in life, a process commonly referred to as "The Atopic March". For example, it has been demonstrated in human cohorts that children with persistent food hypersensitivity early in life have a dramatically increased risk to develop allergic rhinitis (hay fever) or asthma later in childhood (Ostblöm et al 2008). Children with milder forms of food hypersensitivity also have increased risk for development of respiratory allergies but to a lesser degree than children with persistent food hypersensitivity. Therefore, attenuating the severity of food hypersensitivity may be crucial for slowing down the "Atopic March".

In this context the management of allergic episodes and prevention of allergies are, in childhood and infancy, of the highest importance.

The immune system of infants is actively developing all along the few first years of life. Acting on, preventing, avoiding, managing, reducing or modulating the allergic reactions in such young patients can influence their allergic profile short term but also longer term for later in life.

Evidence suggests that infancy may be a critical period in the development of allergies. Mother's milk is recommended for all infants for various reasons. Breastfeeding has especially been reported to decrease the risk of developing allergies in the offspring (Lodge, C J, Breastfeeding and asthma and allergies: a systematic review and meta-analysis, Acta Paediatrica, 2015).

However, in some cases breastfeeding is inadequate or unsuccessful for medical reasons or the mother chooses not to breast feed. Infant formula have been developed for these situations. Fortifiers have also been developed to enrich mother's milk or infant formula with specific ingredients.

Short Chain fatty acids (SCFAs) are especially produced by microbial fermentation of dietary fibres in the colon. Propionate is a SCFA that has been shown to protect against allergic inflammation in the lung and decrease allergic sensitization (presence of total IgE) (Trompette et al., "*Gut Microbiota metabolism of dietary fiber influences allergic airway disease and hematopoiesis*", Nature Medicine, 2013). Allergic sensitization (presence of total IgE) is a marker for increased risk of developing allergic symptoms, thus the decrease shown in total IgE is to be understood as an indication of efficacy of propionate in preventing and/or treating allergy beyond allergic inflammation in the lung, that is, in general.

Increasing propionate is therefore an attractive target to protect against allergy and allergic symptoms. However, orally administered SCFA can be unpalatable.

Alternative solutions more appropriate to infants and young children should therefore be developed.

Human milk oligosaccharides (HMOs) are, collectively, the third largest solid constituents in human milk, after lactose and fat. HMOs usually consist of lactose at the reducing end with a carbohydrate core that often contains a fucose or a sialic acid at the non-reducing end. There are over one hundred milk oligosaccharides that have been isolated and characterized in human milk.

Some compositions using HMO ingredients, such as fucosylated oligosaccharides, lacto-N-tetraose, lacto-N-neotetraose and/or sialylated oligosaccharides, have been described for different health purposes, mainly immune purposes.

However the use of HMOs for the prevention of allergy and allergic symptoms has not been fully explored yet.

There is clearly a need for developing suitable methods to prevent and/or treat allergy, in infants and young children.

There is also a need to deliver such health benefits in a manner that is particularly suitable for the young subjects (infants and young children), in a manner that does not involve a classical pharmaceutical intervention as the infants or young children are particularly fragile.

There is a need to deliver such health benefits in the infants or young children in a manner that does not induce side effects and/or in a manner that is easy to deliver, and well accepted by the parents or health care practitioners.

There is also a need to deliver such benefits in a manner that does keep the cost of such delivery reasonable and affordable by most.

SUMMARY OF THE INVENTION

The present inventors have found that a composition comprising at least one fucosylated oligosaccharide and at least one N-acetylated oligosaccharide can increase colonic propionate production in an animal model.

Since propionate is especially known to protect against allergy, such a composition can therefore advantageously be used to prevent and/or treat allergy symptoms in an infant or a young child.

In a particularly advantageous embodiment, the nutritional composition according to the invention comprises 2'-fucosyllactose (2-FL) and lacto-N-neotetraose (LNnT), and especially 2FL:LNnT in a weight ratio from 1:2 to 2:1.

FIGURES

FIG. 1 represents the propionate production from caecum of mice fed with low-fiber diets and with low-fiber diets enriched with 5% of different tested fibers.

Abbreviations: Pos ctr=positive control; HMO=human milk oligosaccharides, 2FL+LNnT in a weight ratio of 1:1 were tested; PDX=polydextrose.

FIG. 2 represents the ratio of the median of each SCFA of fiber-enriched diet divided by the median of the positive control diet.

Abbreviations: Ctrl pos=positive control; HMO=human milk oligosaccharides, 2FL+LNnT in a weight ratio of 1:1 were tested; PDX=polydextrose.

DETAILED DESCRIPTION OF THE INVENTION

Figure 1:
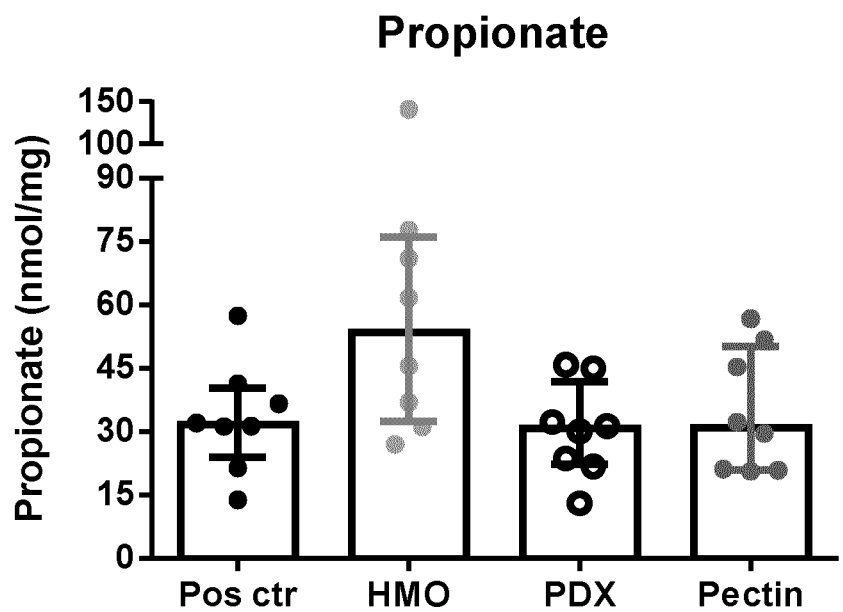

As used herein, the following terms have the following meanings.

The term "infant" means a child under the age of 12 months.

The expression "young child" means a child aged between one and three years, also called toddler.

An "infant or young child born by C-section" means an infant or young child who was delivered by caesarean. It means that the infant or young child was not vaginally delivered.

An "infant or young child vaginally born" means an infant or young child who was vaginally delivered and not delivered by caesarean.

A "preterm" or "premature" means an infant or young child who was not born at term. Generally it refers to an infant or young child born prior 36 weeks of gestation.

The expression "nutritional composition" means a composition which nourishes a subject. This nutritional composition is usually to be taken orally or intravenously. It may include a lipid or fat source, a carbohydrate source and/or a protein source. In a particular embodiment the nutritional composition is a ready-to-drink composition such as a ready-to-drink formula.

In a particular embodiment the composition of the present invention is a hypoallergenic nutritional composition. The expression "hypoallergenic nutritional composition" means a nutritional composition which is unlikely to cause allergic reactions.

In a particular embodiment the nutritional composition of the present invention is a "synthetic nutritional composition". The expression "synthetic nutritional composition" means a mixture obtained by chemical and/or biological means or a mixture comprising components obtained by chemical and/or biological means (including for example purification and separation means), which mixture can be chemically identical to the mixture naturally occurring in mammalian milks or can comprise components which are identical to the components naturally occurring in mammalian milks (i.e. the synthetic nutritional composition is not breast milk).

The expression "infant formula" as used herein refers to a foodstuff intended for particular nutritional use by infants during the first months of life and satisfying by itself the nutritional requirements of this category of person (Article 2(c) of the European Commission Directive 91/321/EEC 2006/141/EC of 22 Dec. 2006 on infant formulae and follow-on formulae). It also refers to a nutritional composition intended for infants and as defined in Codex Alimentarius (Codex STAN 72-1981) and Infant Specialities (incl. Food for Special Medical Purpose). The expression "infant formula" encompasses both "starter infant formula" and "follow-up formula" or "follow-on formula".

A "follow-up formula" or "follow-on formula" is given from the 6th month onwards. It constitutes the principal liquid element in the progressively diversified diet of this category of person.

The expression "baby food" means a foodstuff intended for particular nutritional use by infants or young children during the first years of life.

The expression "infant cereal composition" means a foodstuff intended for particular nutritional use by infants or young children during the first years of life.

The term "fortifier" refers to liquid or solid nutritional compositions suitable for mixing with breast milk or infant formula.

The expression "weaning period" means the period during which the mother's milk or infant formulas are substituted by other food in the diet of an infant or young child.

The expressions "days/weeks/months/years of life", "days/weeks/months/years after birth" and "days/weeks/months/years of birth" can be used interchangeably.

The term "prevention and/or treatment of allergy/allergic response/allergic symptoms/allergic disease" means the prevention and/or the reduction of frequency and/or occurrence and/or severity and/or duration of "allergy" or "allergic response" or "allergic symptoms" or "allergic disease". Occurrence is related to the number of "allergy" or "allergic response" or "allergic symptoms" or "allergic disease". Frequency is related to the number of the same allergy" or "allergic response" or "allergic symptoms" or "allergic disease". This prevention encompasses the reduction of frequency and/or of severity of said "allergy" or "allergic response" or "allergic symptoms" or "allergic disease" later in life. The term "later in life" encompasses the effect after the termination of the intervention.

The expression "later in life" and "in later life" can be used interchangeably. They refer to effects measured in the individual (infant or young child) after the age of some weeks, some months or some years after birth, such as after the age of 6 months after birth, such as after the age of 8 months after birth, such as after the age of 10 months after birth, such as after the age of 1 year after birth, such as after the age of 2 years, preferably after the age of 4 years, more preferably after the age of 5 years, even more preferably after the age of 7 years after birth, or even more, and as a comparison to average observations for subjects of the same age. Preferably it refers to an effect observed after at least 1 year of life, or after at least 2, 5, 7, 10 or 15 years of life. So the expression "later in life" might refer to an observation during infancy, during childhood, during the adolescent period, or during adulthood. Preferably it refers to an observation during childhood, during the adolescent period, or during adulthood. The term "later in life" encompasses the effect after the termination of the intervention.

The expression "health disorder(s)" encompass any health conditions and/or diseases and/or dysfunctions that affect the organism of an individual.

The expression "allergy" or "allergic response" or "allergic symptoms" or "allergic disease" can be used interchangeably. Such terms include, but are not limited to allergic sensitization, food allergy, atopic dermatitis and eczema, wheezing, asthma, allergic rhinitis, rhino-conjunctivitis, eosinophilic esophagitis, hypersensitivity, anaphylaxis, urticaria. Allergy may be developed to different allergens which are all comprised within the scope of this invention; non-limiting examples include proteins derived from food such as cow's milk, eggs, cereals, nuts, or from pollen, from animal dander, from house dust mite.

The term "SCFA" means short chain fatty acid(s).

The expression "increasing propionate production" means that the amount of systemic and/or colonic propionate is higher in an individual fed with the nutritional composition according to the present invention (i.e. comprising at least one fucosylated oligosaccharide and at least one N-acetylated oligosaccharide) in comparison with a standard composition (i.e. a nutritional composition not comprising at least one fucosylated oligosaccharide and at least one N-acetylated oligosaccharide) and/or in comparison with a standard composition supplemented with common fibers like polydextrose or pectin. The propionate production may be measured by techniques known by the skilled person such as by Gas-Liquid Chromatography.

The expression "increasing colonic propionate production" means that the amount of propionate, when measured in the colon (or large intestine) or in a part thereof such as the caecum, is higher in an individual fed with the nutritional composition according to the present invention (i.e. comprising at least one fucosylated oligosaccharide and at least one N-acetylated oligosaccharide) in comparison with a standard composition (i.e. a nutritional composition not comprising at least one fucosylated oligosaccharide and at least one N-acetylated oligosaccharide) and/or in comparison with a standard composition supplemented with common fibers like polydextrose or pectin. The propionate production may be measured by techniques known by the skilled person such as by Gas-Liquid Chromatography.

The "mother's milk" should be understood as the breast milk or the colostrum of the mother.

The term "HMO" or "HMOs" refers to human milk oligosaccharide(s). These carbohydrates are resistant to enzymatic hydrolysis by digestive enzymes (e.g pancreatic and/or brush border), indicating that they may display functions not directly related to their caloric value. It has especially been illustrated that they play a vital role in the early development of infants and young children, such as the maturation of the immune system. Many different kinds of HMOs are found in the human milk. Each individual oligosaccharide is based on a combination of glucose, galactose, sialic acid (N-acetylneuraminic acid), fucose and/or N-acetylglucosamine with many and varied linkages between them, thus accounting for the enormous number of different oligosaccharides in human milk—over 130 such structures have been identified so far. Almost all of them have a lactose moiety at their reducing end while sialic acid and/or fucose (when present) occupy terminal positions at the non-reducing ends. The HMOs can be acidic (e.g. charged sialic acid containing oligosaccharide) or neutral (e.g. fucosylated oligosaccharide).

A "fucosylated oligosaccharide" is an oligosaccharide having a fucose residue. It has a neutral nature. Some examples are 2'-FL (2'-fucosyllactose or 2-fucosyllactose or 2FL or 2-FL), 3-FL (3-fucosyllactose), difucosyllactose, lacto-N-fucopentaose (e.g. lacto-N-fucopentaose I, lacto-N-fucopentaose II, lacto-N-fucopentaose III, lacto-N-fucopentaose V), lacto-N-fucohexaose, lacto-N-difucohexaose I, fucosyllacto-N-hexaose, fucosyllacto-N-neohexaose, difucosyllacto-N-hexaose I, difucosyllacto-N-neohexaose II and any combination thereof.

The expressions "fucosylated oligosaccharides comprising a 2'-fucosyl-epitope" and "2-fucosylated oligosaccharides" encompass fucosylated oligosaccharides with a certain homology of form since they contain a 2'-fucosyl-epitope, therefore a certain homology of function can be expected.

The expression "N-acetylated oligosaccharide(s)" encompasses both "N-acetyl-lactosamine" and "oligosaccharide(s) containing N-acetyl-lactosamine". They are neutral oligosaccharides having an N-acetyl-lactosamine residue. Suitable examples are LNT (lacto-N-tetraose), para-lacto-N-neohexaose (para-LNnH), LNnT (lacto-N-neotetraose) or any combination thereof. Other examples are lacto-N-hexaose, lacto-N-neohexaose, para-lacto-N-hexaose, para-lacto-N-neohexaose, lacto-N-octaose, lacto-N-neooctaose, iso-lacto-N-octaose, para-lacto-N-octaose and lacto-N-decaose.

The expression "at least one fucosylated oligosaccharide" and "at least one N-acetylated oligosaccharide" means "at least one type of fucosylated oligosaccharide" and "at least one type of N-acetylated oligosaccharide".

A "precursor of HMO" is a key compound that intervenes in the manufacture of HMO, such as sialic acid and/or fucose.

A "sialylated oligosaccharide" is a charged sialic acid containing oligosaccharide, i.e. an oligosaccharide having a sialic acid residue. It has an acidic nature. Some examples are 3-SL (3' sialyllactose) and 6-SL (6' sialyllactose).

The expressions "galacto-oligosaccharide", "galactooligosaccharide" and "GOS" can be used interchangeably. They refer to an oligosaccharide comprising two or more galactose molecules which has no charge and no N-acetyl residue (i.e. they are neutral oligosaccharide). In a particular embodiment, said two or more galactose molecules are linked by a $\beta$-1,2, $\beta$-1,3, $\beta$-1,4 or $\beta$-1,6 linkage. In another embodiment, "galacto-oligosaccharide" and "GOS" also include oligosaccharides comprising one galactose molecule and one glucose molecule (i.e. disaccharides) which are linked by a $\beta$-1,2, $\beta$-1,3 or $\beta$-1,6 linkage.

The nutritional composition of the present invention can be in solid form (e.g. powder) or in liquid form. The amount of the various ingredients (e.g. the oligosaccharides) can be expressed in g/100 g of composition on a dry weight basis when it is in a solid form, e.g. a powder, or as a concentration in g/L of the composition when it refers to a liquid form (this latter also encompasses liquid composition that may be obtained from a powder after reconstitution in a liquid such as milk, water . . . , e.g. a reconstituted infant formula or follow-on/follow-up formula or infant cereal product or any other formulation designed for infant nutrition).

The terms "prebiotic", "fibre(s)" and "fiber(s)" can be used interchangeably. They refer to non-digestible carbohydrates that beneficially affect the host by selectively stimulating the growth and/or the activity of healthy bacteria such as bifidobacteria in the colon of humans (Gibson G R, Roberfroid M B. *Dietary modulation of the human colonic microbiota: introducing the concept of prebiotics. J Nutr.* 1995; 125:1401-12).

The term "probiotic" means microbial cell preparations or components of microbial cells with a beneficial effect on the health or well-being of the host. (Salminen S, Ouwehand A. Benno Y. et al. *"Probiotics: how should they be defined"* Trends Food Sci. Technol. 1999:10 107-10). The microbial cells are generally bacteria or yeasts.

The term "cfu" should be understood as colony-forming unit.

All percentages are by weight unless otherwise stated.

In addition, in the context of the invention, the terms "comprising" or "comprises" do not exclude other possible elements. The composition of the present invention, including the many embodiments described herein, can comprise, consist of, or consist essentially of the essential elements and limitations of the invention described herein, as well as any additional or optional ingredients, components, or limitations described herein or otherwise depending on the needs.

Any reference to prior art documents in this specification is not to be considered an admission that such prior art is widely known or forms part of the common general knowledge in the field.

The invention will now be described in further details. It is noted that the various aspects, features, examples and embodiments described in the present application may be compatible and/or combined together.

The present invention therefore refers to a nutritional composition comprising at least one fucosylated oligosaccharide and at least one N-acetylated oligosaccharide, for use in preventing and/or treating allergy symptoms in an infant or a young child, by increasing propionate production, particularly colonic, in said infant or young child.

In one embodiment, the present invention therefore refers to a nutritional composition comprising at least one fucosylated oligosaccharide and at least one N-acetylated oligosaccharide, for use in preventing and/or treating allergy symptoms in an infant or a young child, by increasing colonic propionate production, particularly propionate, in said infant or young child.

Without being bound by theory, the inventors of the present invention believe that the fucosylated oligosaccharide(s) and the N-acetylated oligosaccharide(s) act synergistically to surprisingly provide the above-mentioned health benefits. This particular combination of oligosaccharides would significantly increase the propionate production of an individual and therefore be useful in for use in preventing and/or treating allergy symptoms in an infant or a young child, by increasing propionate production, particularly colonic propionate, in said infant or young children.

The nutritional composition of the present invention comprises at least one fucosylated oligosaccharide. There can be one or several types of fucosylated oligosaccharide(s).

The fucosylated oligosaccharide(s) can indeed be selected from the list comprising 2'-fucosyllactose, 3'fucosyllactose, difucosyllactose, lacto-N-fucopentaose (such as lacto-N-fucopentaose I, lacto-N-fucopentaose II, lacto-N-fucopentaose III, lacto-N-fucopentaose V), lacto-N-fucohexaose, lacto-N-difucohexaose I, fucosyllacto-N-hexaose, fucosyllacto-N-neohexaose (such as fucosyllacto-N-neohexaose I, fucosyllacto-N-neohexaose II), difucosyllacto-N-hexaose I, difuco-lacto-N-neohexaose, difucosyllacto-N-neohexaose I, difucosyllacto-N-neohexaose II, fucosyl-para-Lacto-N-hexaose, tri-fuco-para-Lacto-N-hexaose I and any combination thereof.

In some particular embodiments the fucosylated oligosaccharide comprises a 2'-fucosyl-epitope. It can be for example selected from the list comprising 2'-fucosyllactose, difucosyllactose, lacto-N-fucopentaose, lacto-N-fucohexaose, lacto-N-difucohexaose, fucosyllacto-N-hexaose, fucosyllacto-N-neohexaose, difucosyllacto-N-hexaose difuco-lacto-N-neohexaose, difucosyllacto-N-neohexaose, fucosyl-para-Lacto-N-hexaose and any combination thereof.

In a preferred embodiment, the nutritional composition according to the invention comprises 2'-fucosyllactose (or 2FL, or 2'FL, or 2-FL or 2'-FL). In a particular embodiment, there is no other type of fucosylated oligosaccharide than 2'-fucosyllactose, i.e. the nutritional composition of the invention comprises only 2'-fucosyllactose as fucosylated oligosaccharide.

The fucosylated oligosaccharide(s) may be isolated by chromatography or filtration technology from a natural source such as animal milks. Alternatively, it may be produced by biotechnological means using specific fucosyltransferases and/or fucosidases either through the use of enzyme-based fermentation technology (recombinant or natural enzymes) or microbial fermentation technology. In the latter case, microbes may either express their natural enzymes and substrates or may be engineered to produce respective substrates and enzymes. Single microbial cultures and/or mixed cultures may be used. Fucosylated oligosaccharide formation can be initiated by acceptor substrates starting from any degree of polymerization (DP), from DP=1 onwards. Alternatively, fucosylated oligosaccharides may be produced by chemical synthesis from lactose and free fucose. Fucosylated oligosaccharides are also available for example from Kyowa, Hakko, Kogyo of Japan.

The composition of the present invention also comprises at least one of the N-acetylated oligosaccharide. There can be one or several types of N-acetylated oligosaccharide. The N-acetylated oligosaccharide(s) can be for example lacto-N-tetraose (LNT), lacto-N-neotetraose (LNnT) or any combination thereof. In some particular embodiments the N-acetylated oligosaccharide is lacto-N-neotetraose (LNnT), para-lacto-N-neohexaose (para-LNnH) or any combination thereof. In some particular embodiments the N-acetylated oligosaccharide is LNnT. In some particular embodiments the N-acetylated oligosaccharide is LNT. In some other particular embodiments the N-acetylated oligosaccharide is a mixture of LNT and LNnT. In some particular embodiments the composition comprises both LNT and LNnT in a ratio LNT:LNnT between 5:1 and 1:2, or from 2:1 to 1:1, or from 2:1.2 to 2:1.6.

In a preferred embodiment, the nutritional composition according to the invention comprises lacto-N-neotetraose (LNnT). In a particular embodiment, there is no other type of N-acetylated oligosaccharide than lacto-N-neotetraose (LNnT), i.e. the nutritional composition of the invention comprises only lacto-N-neotetraose (LNnT) as N-acetylated oligosaccharide.

The N-acetylated oligosaccharide(s) may be synthesised chemically by enzymatic transfer of saccharide units from donor moieties to acceptor moieties using glycosyltransferases as described for example in U.S. Pat. No. 5,288,637 and WO 96/10086. Alternatively, LNT and LNnT may be prepared by chemical conversion of Keto-hexoses (e.g. fructose) either free or bound to an oligosaccharide (e.g. lactulose) into N-acetylhexosamine or an N-acetylhexosamine-containing oligosaccharide as described in Wrodnigg, T. M.; Stutz, A. E. (1999) Angew. Chem. Int. Ed. 38:827-828. N-acetyl-lactosamine produced in this way may then be transferred to lactose as the acceptor moiety. The N-acetylated oligosaccharide(s) may also be produced by biotechnological means based on microbial fermentation technology.

In a particularly advantageous embodiment of the present invention, the nutritional composition comprises 2'-fucosyllactose (2FL) and lacto-N-neotetraose (LNnT). In another specific embodiment, the nutritional composition of the present invention comprises an oligosaccharide mixture that consists of 2'-fucosyllactose (2-FL) and lacto-N-neotetraose (LNnT). In other words, the nutritional composition of the invention comprises only 2'-fucosyllactose (2-FL) as fucosylated oligosaccharide and only lacto-N-neotetraose (LNnT) as N-acetylated oligosaccharide.

In some embodiments the fucosylated oligosaccharide(s):N-acetylated oligosaccharide(s) (e.g. 2FL:LNnT) weight ratio in the nutritional composition of the present invention is from 1:10 to 12:1 such as from 1:7 to 10:1 or from 1:5 to 5:1, or from 2:1 to 5:1 or from 1:3 to 3:1, or from 1:2 to 2:1, or from 1:1 to 3:1, or from 1:5 to 1:0.5.

The fucosylated oligosaccharide(s) and the N-acetylated oligosaccharide(s) present into the nutritional composition of the present invention may be in a total amount of from 0.1 to 10 wt %, such as from 0.5 to 7 wt % or from 1 to 5 wt % of the nutritional composition before reconstitution with water. For reconstituted ready-to-drink formula target is from 0.01 to 1%, more preferably 0.05 to 0.7% or 0.1 to 0.5%.

The nutritional composition of the present invention may for example comprise:
- fucosylated oligosaccharide(s) in a total amount of 0.2-5 g/L, for example 0.5-4.5 g/L or 1-4 g/L of the composition, or in a total amount of 0.13-3.48 g/100 g, for example 0.34-3.13 g/100 g or 0.69-2.78 g/100 g of composition on a dry weight basis; and/or
- N-acetylated oligosaccharide(s) in a total amount of 0.05-5 g/L, for example 0.1-2 g/L or 0.1-1 g/L of the composition, or in a total amount of 0.0.03-3.48 g/100 g, for example 0.07-1.4 g/100 g or 0.07-0.7 g/100 g of composition on a dry weight basis.

The nutritional composition according to the present invention may also comprise at least another oligosaccharide(s) (i.e. other than the fucosylated oligosaccharide(s) and N-acetylated oligosaccharide(s) necessarily present in the composition) and/or at least a fiber(s) and/or at least a precursor(s) of human milk oligosaccharide(s). The other oligosaccharide and/or fiber and/or precursor may be selected from the list comprising galacto-oligosaccharides (GOS), fructo-oligosaccharides (FOS), inulin, xylooligosaccharides (XOS), polydextrose, sialylated oligosaccharides, sialic acid, fucose and any combination thereof. They may be in an amount between 0 and 10% by weight of composition.

Suitable commercial products that can be used in addition to the oligosaccharides comprised in the oligosaccharide mixture to prepare the nutritional compositions according to the invention include combinations of FOS with inulin such as the product sold by BENEO under the trademark Orafti, or polydextrose sold by Tate & Lyle under the trademark STA-LITE®.

In a particular embodiment, the composition according to the invention can comprise sialylated oligosaccharide(s). There can be one or several sialylated oligosaccharide(s). The sialylated oligosaccharide(s) can be selected from the group comprising 3' sialyllactose (3-SL), 6' sialyllactose (6-SL), and any combination thereof. In some embodiments of the invention the composition comprises 3-SL and 6-SL. In some particular embodiments the ratio between 3'-sialyllactose (3-SL) and 6'-sialyllactose (6-SL) can be in the range between 5:1 and 1:10, or from 3:1 and 1:1, or from 1:1 to 1:10. In some specific embodiments the sialylated oligosaccharide of the composition is 6' sialyllactose (6-SL).

The sialylated oligosaccharide(s) may be isolated by chromatographic or filtration technology from a natural source such as animal milks. Alternatively, they may be produced by biotechnological means using specific sialyltransferases or sialidases, neuraminidases, either by an enzyme based fermentation technology (recombinant or natural enzymes), by chemical synthesis or by a microbial fermentation technology. In the latter case microbes may either express their natural enzymes and substrates or may be engineered to produce respective substrates and enzymes. Single microbial cultures or mixed cultures may be used. Sialyl-oligosaccharide formation can be initiated by acceptor substrates starting from any degree of polymerisation (DP), from DP=1 onwards. Alternatively, sialyllactoses may be produced by chemical synthesis from lactose and free N'-acetylneuraminic acid (sialic acid). Sialyllactoses are also commercially available for example from Kyowa Hakko Kogyo of Japan.

In particular examples the composition may comprise sialylated oligosaccharide(s) in a total amount of from 0.05 to 5 g/L of, for example from 0.1 to 4 g/L, or from 0.3 to 2 g/L of the composition, or in a total amount of from 0.03 to 3.5 g/100 g, for example from 0.1 to 2 g or from 0.2 to 1 g/100 g of composition on a dry weight basis.

In a particular embodiment, the nutritional composition can also contain at least one BMO (bovine milk oligosaccharide). In a particular embodiment, the nutritional composition may additionally comprise an oligosaccharide mixture ("BMOS") that comprises from 0.1 to 4.0 wt % of N-acetylated oligosaccharide(s), from 92.0 to 99.5 wt % of the galacto-oligosaccharide(s) and from 0.2 to 4.0 wt % of the sialylated oligosaccharide(s). WO2006087391 and WO2012160080 provide some examples of production of a BMOs mixture.

In some particular embodiments of the present invention, the nutritional composition does not contain any sialylated oligosaccharide(s), any GOS and/or any bovine milk oligosaccharide.

The composition according to the present invention may optionally also comprise at least one precursor of human milk oligosaccharide. There can be one or several precursor(s). For example the precursor of human milk oligosaccharide is sialic acid, fucose or a mixture thereof. In some particular embodiments the composition comprises sialic acid. In particular examples the composition comprises from 0 to 3 g/L of precursor(s) of human milk oligosaccharide, or from 0 to 2 g/L, or from 0 to 1 g/L, or from 0 to 0.7 g/L, or from 0 to 0.5 g/L or from 0 to 0.3 g/L, or from 0 to 0.2 g/L of precursor(s) of human milk oligosaccharide.

The composition according to the invention can contain from 0 to 2.1 g of precursor(s) of human milk oligosaccharide per 100 g of composition on a dry weight basis, e.g. from 0 to 1.5 g or from 0 to 0.8 g or from 0 to 0.15 g of precursor(s) of human milk oligosaccharide per 100 g of composition on a dry weight basis.

The nutritional composition of the present invention can further comprise at least one probiotic (or probiotic strain), such as a probiotic bacterial strain.

The probiotic microorganisms most commonly used are principally bacteria and yeasts of the following genera: *Lactobacillus* spp., *Streptococcus* spp., *Enterococcus* spp., *Bifidobacterium* spp. and *Saccharomyces* spp.

In some particular embodiments, the probiotic is a probiotic bacterial strain. In some specific embodiments, it is particularly *Bifidobacteria* and/or *Lactobacilli*.

Suitable probiotic bacterial strains include *Lactobacillus rhamnosus* ATCC 53103 available from Valio Oy of Finland under the trademark LGG, *Lactobacillus rhamnosus* CGMCC 1.3724, *Lactobacillus paracasei* CNCM 1-2116, *Lactobacillus johnsonii* CNCM I-1225, *Streptococcus salivarius* DSM 13084 sold by BLIS Technologies Limited of New Zealand under the designation KI2, *Bifidobacterium lactis* CNCM 1-3446 sold inter alia by the Christian Hansen company of Denmark under the trademark Bb 12, *Bifidobacterium longum* ATCC BAA-999 sold by Morinaga Milk Industry Co. Ltd. of Japan under the trademark BB536, *Bifidobacterium breve* sold by Danisco under the trademark Bb-03, *Bifidobacterium breve* sold by Morinaga under the trade mark M-16V, *Bifidobacterium infantis* sold by Procter & Gamble Co. under the trademark Bifantis and *Bifidobacterium breve* sold by Institut Rosell (Lallemand) under the trademark R0070.

The nutritional composition according to the invention may contain from 10e3 to 10e12 cfu of probiotic strain, more preferably between 10e7 and 10e12 cfu such as between 10e8 and 10e10 cfu of probiotic strain per g of composition on a dry weight basis.

In one embodiment the probiotics are viable. In another embodiment the probiotics are non-replicating or inactivated. There may be both viable probiotics and inactivated probiotics in some other embodiments.

The nutritional composition of the invention can further comprise at least one phage (bacteriophage) or a mixture of phages, preferably directed against pathogenic *Streptococci, Haemophilus, Moraxella* and *Staphylococci*.

The nutritional composition according to the invention can be for example an infant formula, a starter infant formula, a follow-on or follow-up formula, a baby food, an infant cereal composition, a fortifier such as a human milk fortifier, or a supplement. In some particular embodiments, the composition of the invention is an infant formula, a fortifier or a supplement that may be intended for the first 4 or 6 months of age. In a preferred embodiment the nutritional composition of the invention is an infant formula.

In some other embodiments the nutritional composition of the present invention is a fortifier. The fortifier can be a breast milk fortifier (e.g. a human milk fortifier) or a formula fortifier such as an infant formula fortifier or a follow-on/follow-up formula fortifier.

When the nutritional composition is a supplement, it can be provided in the form of unit doses.

The nutritional composition of the present invention can be in solid (e.g. powder), liquid or gelatinous form.

The nutritional composition according to the invention generally contains a protein source. The protein can be in an amount of from 1.5 to 3 g per 100 kcal. In some embodiments, especially when the composition is intended for premature infants, the protein amount can be between 2.4 and 4 g/100 kcal or more than 3.6 g/100 kcal. In some other embodiments the protein amount can be below 2.0 g per 100 kcal, e.g. between 1.8 to 2 g/100 kcal, or in an amount below 1.8 g per 100 kcal.

The type of protein is not believed to be critical to the present invention provided that the minimum requirements for essential amino acid content are met and satisfactory growth is ensured. Thus, protein sources based on whey, casein and mixtures thereof may be used as well as protein sources based on soy. As far as whey proteins are concerned, the protein source may be based on acid whey or sweet whey or mixtures thereof and may include alpha-lactalbumin and beta-lactoglobulin in any desired proportions.

In some advantageous embodiments the protein source is whey predominant (i.e. more than 50% of proteins are coming from whey proteins, such as 60% or 70%).

The proteins may be intact or hydrolysed or a mixture of intact and hydrolysed proteins. By the term "intact" is meant that the main part of the proteins are intact, i.e. the molecular structure is not altered, for example at least 80% of the proteins are not altered, such as at least 85% of the proteins are not altered, preferably at least 90% of the proteins are not altered, even more preferably at least 95% of the proteins are not altered, such as at least 98% of the proteins are not altered. In a particular embodiment, 100% of the proteins are not altered.

The term "hydrolysed" means in the context of the present invention a protein which has been hydrolysed or broken down into its component amino acids.

The proteins may be either fully or partially hydrolysed. It may be desirable to supply partially hydrolysed proteins (degree of hydrolysis between 2 and 20%), for example for infants or young children believed to be at risk of developing cow's milk allergy. If hydrolysed proteins are required, the hydrolysis process may be carried out as desired and as is known in the art. For example, whey protein hydrolysates may be prepared by enzymatically hydrolysing the whey fraction in one or more steps. If the whey fraction used as the starting material is substantially lactose free, it is found that the protein suffers much less lysine blockage during the hydrolysis process. This enables the extent of lysine blockage to be reduced from about 15% by weight of total lysine to less than about 10% by weight of lysine; for example about 7% by weight of lysine which greatly improves the nutritional quality of the protein source.

In an embodiment of the invention at least 70% of the proteins are hydrolysed, preferably at least 80% of the proteins are hydrolysed, such as at least 85% of the proteins are hydrolysed, even more preferably at least 90% of the proteins are hydrolysed, such as at least 95% of the proteins are hydrolysed, particularly at least 98% of the proteins are hydrolysed. In a particular embodiment, 100% of the proteins are hydrolysed.

In one particular embodiment the proteins of the nutritional composition are hydrolyzed, fully hydrolyzed or partially hydrolyzed. The degree of hydrolysis (DH) of the protein can be between 8 and 40, or between 20 and 60 or between 20 and 80 or more than 10, 20, 40, 60, 80 or 90.

In a particular embodiment the nutritional composition according to the invention is a hypoallergenic composition. In another particular embodiment the composition according to the invention is a hypoallergenic nutritional composition.

The nutritional composition according to the present invention generally contains a carbohydrate source. This is particularly preferable in the case where the nutritional composition of the invention is an infant formula. In this case, any carbohydrate source conventionally found in infant formulae such as lactose, sucrose, saccharose, maltodextrin, starch and mixtures thereof may be used although one of the preferred sources of carbohydrates is lactose.

The nutritional composition according to the present invention generally contains a source of lipids. This is particularly relevant if the nutritional composition of the invention is an infant formula. In this case, the lipid source may be any lipid or fat which is suitable for use in infant formulae. Some suitable fat sources include palm oil, high oleic sunflower oil and high oleic safflower oil. The essential fatty acids linoleic and α-linolenic acid may also be added, as well small amounts of oils containing high quantities of preformed arachidonic acid and docosahexaenoic acid such as fish oils or microbial oils. The fat source may have a ratio of n-6 to n-3 fatty acids of about 5:1 to about 15:1; for example about 8:1 to about 10:1.

The nutritional composition of the invention may also contain all vitamins and minerals understood to be essential in the daily diet and in nutritionally significant amounts. Minimum requirements have been established for certain vitamins and minerals. Examples of minerals, vitamins and other nutrients optionally present in the composition of the invention include vitamin A, vitamin B1, vitamin B2, vitamin B6, vitamin B12, vitamin E, vitamin K, vitamin C, vitamin D, folic acid, inositol, niacin, biotin, pantothenic acid, choline, calcium, phosphorous, iodine, iron, magnesium, copper, zinc, manganese, chlorine, potassium, sodium, selenium, chromium, molybdenum, taurine, and L-carnitine. Minerals are usually added in salt form. The presence and amounts of specific minerals and other vitamins will vary depending on the intended population.

If necessary, the nutritional composition of the invention may contain emulsifiers and stabilisers such as soy, lecithin, citric acid esters of mono- and diglycerides, and the like.

The nutritional composition of the invention may also contain other substances which may have a beneficial effect such as lactoferrin, nucleotides, nucleosides, and the like.

The nutritional composition of the invention may also contain carotenoid(s). In some particular embodiments of the invention, the nutritional composition of the invention does not comprise any carotenoid.

The nutritional composition according to the invention may be prepared in any suitable manner. A composition will now be described by way of example.

For example, a formula such as an infant formula may be prepared by blending together the protein source, the carbohydrate source and the fat source in appropriate proportions. If used, the emulsifiers may be included at this point. The vitamins and minerals may be added at this point but they are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture. The temperature of the water is conveniently in the range between about 50° C. and about 80° C. to aid dispersal of the ingredients. Commercially available liquefiers may be used to form the liquid mixture.

The fucosylated oligosaccharide(s) and the N-acetylated oligosaccharide(s) may be added at this stage, especially if the final product is to have a liquid form. If the final product is to be a powder, they may likewise be added at this stage if desired.

The liquid mixture is then homogenised, for example in two stages.

The liquid mixture may then be thermally treated to reduce bacterial loads, by rapidly heating the liquid mixture to a temperature in the range between about 80° C. and about 150° C. for a duration between about 5 seconds and about 5 minutes, for example. This may be carried out by means of steam injection, an autoclave or a heat exchanger, for example a plate heat exchanger.

Then, the liquid mixture may be cooled to between about 60° C. and about 85° C. for example by flash cooling. The liquid mixture may then be again homogenised, for example in two stages between about 10 MPa and about 30 MPa in the first stage and between about 2 MPa and about 10 MPa in the second stage. The homogenised mixture may then be further cooled to add any heat sensitive components, such as vitamins and minerals. The pH and solids content of the homogenised mixture are conveniently adjusted at this point.

If the final product is to be a powder, the homogenised mixture is transferred to a suitable drying apparatus such as a spray dryer or freeze dryer and converted to powder. The powder should have a moisture content of less than about 5% by weight. The fucosylated oligosaccharide(s) and the N-acetylated oligosaccharide(s) may also or alternatively be added at this stage by dry-mixing or by blending them in a syrup form of crystals, along with the probiotic strain(s) (if used), and the mixture is spray-dried or freeze-dried.

If a liquid composition is preferred, the homogenised mixture may be sterilised then aseptically filled into suitable containers or may be first filled into the containers and then retorted.

In another embodiment, the composition of the invention may be a supplement.

The supplement may be in the form of tablets, capsules, pastilles or a liquid for example. The supplement may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents and gel forming agents. The supplement may also contain conventional pharmaceutical additives and adjuvants, excipients and diluents, including, but not limited to, water, gelatine of any origin, vegetable gums, lignin-sulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like.

Further, the supplement may contain an organic or inorganic carrier material suitable for oral or parenteral administration as well as vitamins, minerals trace elements and other micronutrients in accordance with the recommendations of Government bodies such as the USRDA.

The nutritional composition according to the invention is for use in infants or young children. The infants or young children may be born term or preterm. In a particular embodiment the nutritional composition of the invention is for use in infants or young children that were born preterm.

The nutritional composition of the present invention may also be used in an infant or a young child that was born by C-section or that was vaginally delivered.

In some embodiments the nutritional composition according to the invention can be for use before and/or during the weaning period.

In some embodiments the nutritional composition according to the invention is for use in infants or young children at risk of developing allergy. In some embodiments the nutritional composition of the present invention is for use in infants or young children born from allergic women. Indeed, scientific evidence continues to suggest that infants born to allergic mothers have a greater risk of becoming allergic later in life than infants born to mothers who are not allergic.

The nutritional composition can be administered (or given or fed) at an age and for a period that depends on the possibilities and needs.

Since the nutritional composition is also used for prevention purposes (prevention of a later in life health disorder), it can be for example given immediately after birth of the infants. The composition of the invention can also be given during the first week of life of the infant, or during the first 2 weeks of life, or during the first 3 weeks of life, or during the first month of life, or during the first 2 months of life, or during the first 3 months of life, or during the first 4 months of life, or during the first 6 months of life, or during the first 8 months of life, or during the first 10 months of life, or during the first year of life, or during the first two years of life or even more. In some particularly advantageous embodiments of the invention, the nutritional composition is given (or administered) to an infant within the first 4 or 6 months of birth of said infant.

In some other embodiments, the nutritional composition of the invention is given few days (e.g. 1, 2, 3, 5, 10, 15, 20 . . . ), or few weeks (e.g. 1, 2, 3, 4, 5, 6, 7, 8, 9, 10 . . . ), or few months (e.g. 1, 2, 3, 4, 5, 6, 7, 8, 9, 10 . . . ) after birth. This may be especially the case when the infant is premature, but not necessarily.

In one embodiment the composition of the invention is given to the infant or young child as a supplementary composition to the mother's milk. In some embodiments the infant or young child receives the mother's milk during at least the first 2 weeks, first 1, 2, 4, or 6 months. In one embodiment the nutritional composition of the invention is given to the infant or young child after such period of mother's nutrition, or is given together with such period of mother's milk nutrition. In another embodiment the composition is given to the infant or young child as the sole or primary nutritional composition during at least one period of time, e.g. after the $1^{st}$, $2^{nd}$ or $4^{th}$ month of life, during at least 1, 2, 4 or 6 months.

In one embodiment the nutritional composition of the invention is a complete nutritional composition (fulfilling all or most of the nutritional needs of the subject). In another embodiment the nutrition composition is a supplement or a fortifier intended for example to supplement human milk or to supplement an infant formula or a follow-on formula.

The present inventors have found that a specific HMOs intervention in an animal model significantly increased propionate production in the caecum (a part of the colon) of the animal.

As mentioned in the background section, propionate is known to protect against allergy.

The nutritional composition according to the present invention would therefore be useful in preventing and/or treating allergy symptoms in an infant or a young child, by increasing propionate production, particularly colonic propionate production, in said infant or young children.

The health benefits targeted in the present invention may be obtained with the nutritional composition by increasing colonic propionate production in said infant or young child, especially the propionate production in the caecum. In a particular embodiment the propionate production is measured by Gas-Liquid Chromatography and it can be expressed in nmol/mg dry weight.

In a particular embodiment, the colonic propionate production is increased by at least 10%, or at least 15% or at least 20% or at least 30% or at least 40% or at least 50% or at least 60% in comparison to the colonic propionate production obtained with a nutritional composition without at least one fucosylated oligosaccharide and at least one N-acetylated oligosaccharide.

In a particular embodiment, the colonic propionate production is increased by at least 10%, or at least 15% or at least 20% or at least 30% or at least 40% or at least 50% or at least 60% or at least 70% in comparison to the colonic propionate production obtained with a nutritional composition supplemented with common fibers like polydextrose or pectin.

This represents a new clinical situation where prevention of allergy symptoms can be targeted in a new way.

Other Objects:

Another object of the present invention is the use of at least one fucosylated oligosaccharide and at least one N-acetylated oligosaccharide in the preparation of a nutritional composition for preventing and/or treating allergy symptoms in an infant or a young child, by increasing propionate production, in particular colonic propionate production in said infant or young children.

Another object of the present invention is a pharmaceutical composition comprising at least one fucosylated oligosaccharide and at least one N-acetylated oligosaccharide for use in preventing and/or treating allergy symptoms in an infant or a young child, by increasing propionate production, in particular colonic propionate production, in said infant or young children.

Another object of the present invention is the use of at least one fucosylated oligosaccharide and at least one N-acetylated oligosaccharide for preventing and/or treating allergy symptoms in an infant or a young child, by increasing propionate production, in particular colonic propionate production, in said infant or young children.

Another object of the present invention refers to a method for preventing and/or treating allergy symptoms in an infant or a young child, by increasing propionate production, in particular colonic propionate production, in said infant or young child, said method comprising administering to said infant or young child a nutritional composition comprising at least one fucosylated oligosaccharide and at least one N-acetylated oligosaccharide.

The different embodiments, details and examples previously described in the specification (e.g. related to the types and amounts of oligosaccharide, the nutritional composition, the administration, the targeted population . . . ) also apply to all these other objects.

EXAMPLES

The following examples illustrate some specific embodiments of the composition for use according to the present invention. The examples are given solely for the purpose of illustration and are not to be construed as limitations of the present invention, as many variations thereof are possible without departing from the spirit of the invention.

Example 1

An example of the composition of a nutritional composition (e.g. an infant formula) according to the present invention is given in the below table 1. This composition is given by way of illustration only.

TABLE 1 an example of the composition of a nutritional composition (e.g. an infant formula) according to the present invention

| Nutrients | per 100 kcal | per litre |
|---|---|---|
| Energy (kcal) | 100 | 670 |
| Protein (g) | 1.83 | 12.3 |
| Fat (g) | 5.3 | 35.7 |
| Linoleic acid (g) | 0.79 | 5.3 |
| α-Linolenic acid (mg) | 101 | 675 |

TABLE 1-continued an example of the composition of a nutritional composition
(e.g. an infant formula) according to the present invention

| Nutrients | | per 100 kcal | per litre |
|---|---|---|---|
| Lactose (g) | | 11.2 | 74.7 |
| Minerals (g) | | 0.37 | 2.5 |
| Na (mg) | | 23 | 150 |
| K (mg) | | 89 | 590 |
| Cl (mg) | | 64 | 430 |
| Ca (mg) | | 62 | 410 |
| P (mg) | | 31 | 210 |
| Mg (mg) | | 7 | 50 |
| Mn (µg) | | 8 | 50 |
| Se (µg) | | 2 | 13 |
| Vitamin A (µg RE) | | 105 | 700 |
| Vitamin D (µg) | | 1.5 | 10 |
| Vitamin E (mg TE) | | 0.8 | 5.4 |
| Vitamin K1 (µg) | | 8 | 54 |
| Vitamin C (mg) | | 10 | 67 |
| Vitamin B1 (mg) | | 0.07 | 0.47 |
| Vitamin B2 (mg) | | 0.15 | 1.0 |
| Niacin (mg) | | 1 | 6.7 |
| Vitamin B6 (mg) | | 0.075 | 0.50 |
| Folic acid (µg) | | 9 | 60 |
| Pantothenic acid (mg) | | 0.45 | 3 |
| Vitamin B12 (µg) | | 0.3 | 2 |
| Biotin (µg) | | 2.2 | 15 |
| Choline (mg) | | 10 | 67 |
| Fe (mg) | | 1.2 | 8 |
| I (µg) | | 15 | 100 |
| Cu (mg) | | 0.06 | 0.4 |
| Zn (mg) | | 0.75 | 5 |
| Oligosaccharides | 2FL (g) | 0.15 | 1 |
| (HMOs) | LNnT (g) | 0.075 | 0.5 |

Example 2

Description of the Study 5 week old females BALB/cByJ CRL mice from Charles River were split into several groups and fed during 6 weeks based on the following protocol:

Week 1: low-fiber diet (composition is detailed in table 2) for all groups

Weeks 2 to 6:

Control group (group A): low-fiber diet (same as for week 1)

Test groups (groups B-D): low-fiber diet (same as for week 1) supplemented with 5 wt % of a tested fiber (5% of the total low fiber diet was replaced by 5% of a tested fiber)

TABLE 2 composition of the low fiber diet

| Major Nutrients | |
|---|---|
| Dry matter | 93.9% |
| Crude protein | 18.0% |
| Crude fat | 5.0% |
| Crude fiber | 0.3% |
| Crude ash | 3.5% |
| Nitrogen-free extract (NFE) | 67.1% |
| Gross energy | 17.7 MJ/kg |
| Metabol. energy | 16.1 MJ/kg |
| Starch | 42.5% |
| Amino acids | |
| Arginine | 0.76% |
| Lysine | 1.66% |
| Methionine | 0.60% |
| Methionine + cystine | 0.97% |
| Tryptophan | 0.28% |

TABLE 2-continued composition of the low fiber diet

| | |
|---|---|
| Threonine | 0.92% |
| Major mineral elements | |
| Calcium | 0.62% |
| Phosphorus | 0.33% |
| Magnesium | 0.06% |
| Sodium | 0.24% |
| Potassium | 0.41% |
| Chlorine | 0.58% |
| Trace elements | |
| Iron | 50 mg/kg |
| Zinc | 37 mg/kg |
| Copper | 6 mg/kg |
| Iodine | 0.6 mg/kg |
| Manganese | 12 mg/kg |
| Selenium | 0.22 mg/kg |
| Vitamins added | |
| Vitamin A | 4'000 IE|UI|IU/kg |
| Vitamin D3 | 1'000 IE|UI|IU/kg |
| Vitamin E | 100 mg/kg |
| Vitamin K3 | 4 mg/kg |
| Vitamin B1 | 5 mg/kg |
| Vitamin B2 | 6 mg/kg |
| Vitamin B6 | 6 mg/kg |
| Vitamin B12 | 0.05 mg/kg |
| Nicotinic acid | 32 mg/kg |
| Pantothenic acid | 16 mg/kg |
| Folic acid | 2 mg/kg |
| Biotin | 0.2 mg/kg |
| Choline | 998 mg/kg |

The following fibers were tested:

HMO=human milk oligosaccharides. 2FL+LNnT were tested in a weight ratio 1:1

PDX=polydextrose

Pectin

Table 3 provides a summary of the different tested groups and diets.

TABLE 3 tested groups and diets of the study

| Group | Group label | Diet | Sample size |
|---|---|---|---|
| A | Pos ctr or Ctrl pos | Low-fiber diet | 8 |
| B | HMO | Low-fiber diet + 5 wt % HMOs (=2FL + LNnT in a weight ratio of 1:1) | 8 |
| C | PDX | Low-fiber diet + 5 wt % polydextrose | 8 |
| D | Pectin | Low-fiber diet + 5 wt % pectin | 8 |

After 6 weeks, the animals of each group were sacrificed and the content from caecum was collected. The SCFA production were measured by Gas-Liquid Chromatography (GLC; amounts of SCFA in nmol/mg dry weight). The following SCFA were measured: propionate, butyrate, valerate and acetate.

The measure was made based on the following protocol: SCFA in an acid solution (pH 2.0 to 3.0) were separated on a GLC column coated with a polar stationary phase. This allowed for minimal preparation of the sample (no derivatisation) and straightforward basic FID detection. SCFA were extracted from caecum using an acid phosphate buffer containing HgCl2 for inactivation of any residual bacterial activity and an internal standard (2,2 Dimethyl-butyric acid) for GLC analysis. After centrifugation, the sterile-filtered supernatant was ready for analysis by GLC. SCFA were measured simultaneously.

Median ratio values were calculated in order to compare the different fiber-enriched diets on SCFA production.

Findings

The production of propionate by HMO enriched diet was significantly increased (see FIG. 1). Its production was increased by around 69% in comparison to the positive control. Its production was increased by 73 and 75% in comparison to the pectin and PDX, respectively. This is very surprising since pectin is usually seen as a high-inducer of SCFA (Stark et al, J Nutr. 1993, In vitro production of short-chain fatty acids by bacterial fermentation of dietary fiber compared with effects of those fibers on hepatic sterol synthesis in rats; Yang et al, Anaerobe, 2013, In vitro characterization of the impact of selected dietary fibers on fecal microbiota composition and short chain fatty acid production).

Figure 2:
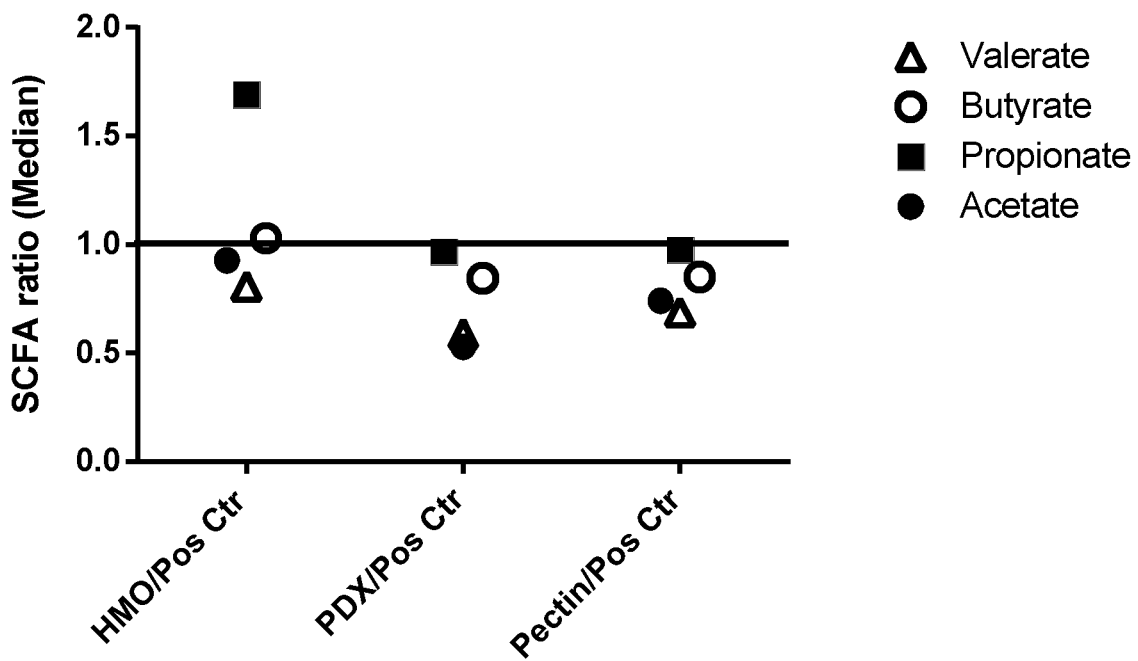

FIG. 2 represents the ratio of the median of each tested SCFA of each fiber-enriched diet divided by the median of the positive control diet (i.e. low-fiber diet only). A ratio of 1 (black line) means that there is no difference between the enriched diet and the control diet. A ratio below 1 means that the corresponding SCFA is higher in the control diet when compared to the fiber-enriched diet whereas a ratio above a means that the corresponding SCFA is higher with the fiber-enriched diet than the control.

The PDX and Pectin enriched diets induced less SCFA release of all kinds. On the contrary the HMO enriched diets induced more propionate release than the low-fiber diet. The HMO-enriched diet was the only one to promote the propionate with a so large difference contrary to the other kinds of SCFA, and contrary to the other tested fibers.

The inventors therefore surprisingly found that mice fed with a composition comprising at least one fucosylated oligosaccharide and at least one N-acetylated oligosaccharide were having a significantly higher caecal (and therefore colonic) propionate production. Due to the known properties of propionate especially on allergy prevention and treatment, a composition comprising at least one fucosylated oligosaccharide and at least one N-acetylated oligosaccharide would therefore be efficient in infants or young children for use in preventing and/or treating allergy symptoms.

Example 3

Methods:

5-8 weeks old female Balb/c mice are sensitized by epicutaneous application of 50-200 μl of an *aspergillus* allergenic extract. A small part of the back of the mouse are shaved. A patch of sterile cotton gauze (1×1 cm) with the allergen is secured to the skin with a bio-occlusive transparent dressing and a Band-Aid. The patch remains on the skin for sensitization periods of 7 consecutive days till it falls or is removed at day 8. The procedure is repeated 2 times with 2 weeks rest in between.

Few days after the last sensitizations, the mice are exposed to 100 ul of allergen by applying a drop in each of in the nostrils.

HMO (more specifically a mix of 2FL and LNnt 2:1) are incorporated to a low fiber diet in the HMO group to a level of 5%. Control diet in other group is adjusted for volume and calories with maltodextrin and cellulose.

Diet started 3 week prior the first sensitization and continue during the whole experiment. Feces were collected after 3 weeks feeding and before the first sensitization occurred. Upon harvest, cecum and blood was collected and immunoglobulin were measured by ELISA as previously described in Holvoet et al (Holvoet S. Allergy 2016 December; 71(12):1753-1761): Specific IgE levels were quantified as follows: *Aspergillus* mold allergen (Greer Laboratories) was re-suspended in distilled water containing anti protease (Sigma) and Triton X100 (Sigma). This solution was sonicated for 5 min in ice and centrifuged at 1000 rpm for 10 min. Upper phase was collected and total protein content was measured with BCA protein assay kit (Thermo Scientific; Zug, Switzerland) according to the manufacturer's protocol. *Aspergillus* total protein was labelled with Digoxigenin-3-O-methylcarbonyl-e-aminocaproic acid-N-hydroxysuccinimide ester (DIG; Roche, Basel, Switzerland) following the manufacture's protocol. 96 well plates were coated with 100 μl of 2 μg/ml rat anti mouse IgE (BD-Bioscience) in carbonate buffer and incubated overnight at 4° C. Plates were washed in PBS 0.05% tween and blocked with 200 μL PBS containing 10% fetal calf serum (FCS; Bioconcept), for 1 h at room temperature. Diluted sera were incubated 2 h at room temperature. After washing, DIG labeled antigen was incubated for 90 min at room temperature. Plates were washed and incubated with HRP-labeled anti-DIG antibody (Roche, Switzerland) 1 h at room temperature. Revelation was performed with TMB and reaction was stopped with 1N HCl (Merck). Plates were read at 450 nm and results are expressed in OD.

Figure 3:
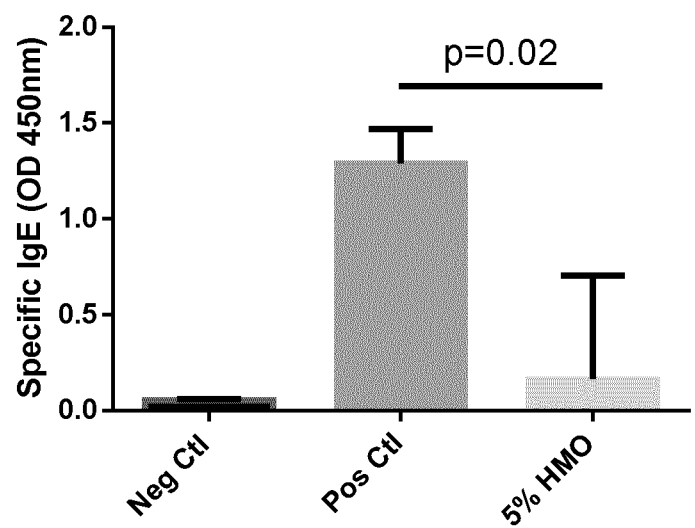
FIG. 3 represents IgE levels measured in mice from the different groups of the experiments reported in Example 3.

Specific IgE levels measured in mice from the different groups of the experiments are reported in FIG. 3.

Colonic propionate levels were measure as followed. Propionate present in the ceacum and feces of the mice fed HMOs were analyzed by gas chromatography coupled to a mass spectrometer (GC-MS), from Agilent Technologies 6890 series XL MSD 5975 C (Santa Clara, Calif.), after a ionization with an electronic impact source. Briefly, coecum and feces were first homogenized in a solution of orthophosphoric acid and Mercury D 3 acetate, corresponding to 4 times the weight of feces. Samples were them homogenized with glass beads for 20 min with a multivortex. Preparation were centrifuged at 2,000 g for 15 min at 4° C. Supernatant were collected and weighted. Ten microliters of HCl 37% and 3 ml of chloroform were added and homogenized for 20 min. After centrifugation 10 min at 1,800 g 4° C. the upper layer was eliminated. Add 10 ul of T-butyldimethylsilylimidazole was added and sample was heated at 60° C. for 30 min then cool down before being injected. Freeze drying to determinate humidity rate and humidity content was used for the calculation of SCFA per gram of dry material.

Figure 4:
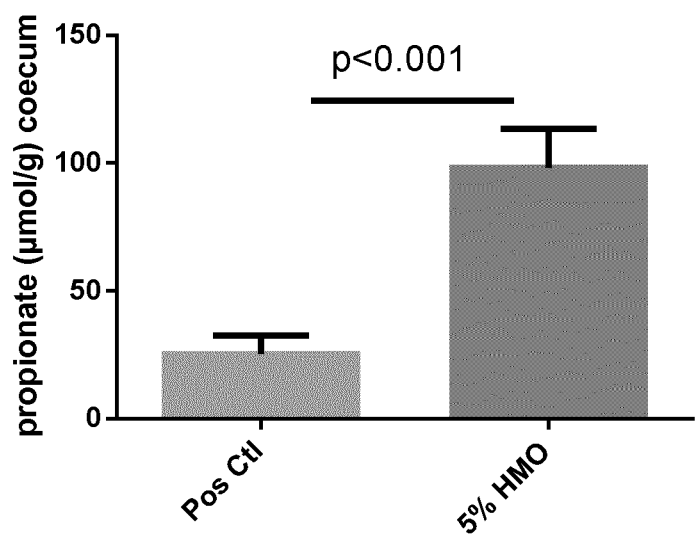
FIG. 4 represents caecum propionate levels measured in mice from the different groups of the experiment reported in Example 3.
Figure 5:
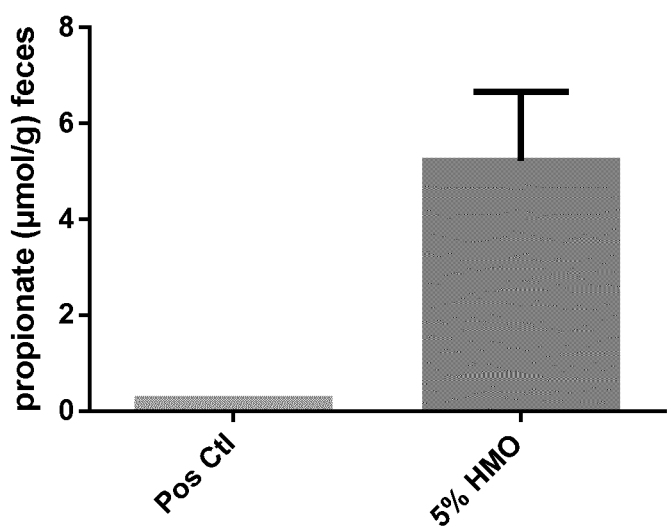
FIG. 5 represents propionate levels in the feces of mice from the different groups of the experiment reported in Example 3.

Specific SFCA levels measured in mice from the different groups of the experiments are reported in FIGS. 4 and 5.

Results:

FIGS. 4 and 5 show a significant increase in propionate when the mice are supplemented with HMO. In this mice, specific IgE levels were significantly lower than the positive control that did not received the HMO supplementation highlighting the association between colonic propionate increase and decrease of allergic sensitization, based on IgE measurement.

The invention claimed is:

1. A method of reducing at least one of a frequency, an occurrence, a severity or a duration of and/or treating allergy symptoms in an infant or a young child in need thereof by increasing colonic propionate production in the infant or young child, the method comprising administering to the infant or young child a nutritional composition comprising at least one fucosylated oligosaccharide comprising 2'-fucosyllactose (2'FL) and at least one N-acetylated oligosaccharide comprising lacto-N-neotetraose (LNnT), wherein the nutritional composition does not include galacto-oligosaccharides (GOS), a total amount of the at least one fucosylated oligosaccharide and the at least one N-acetylated oligosaccharide is 0.1 wt. % to 10 wt. % of the nutritional composition, a total amount of the at least one fucosylated oligosaccharide is 2-4 g/L of the nutritional composition, and a total amount of the at least one N-acetylated oligosaccharide is 0.1-2 g/L of the nutritional composition, the nutritional composition is administered to the infant or young child in an amount effective to increase the colonic propionate production in the infant or young child, and the infant or young child was born by C-section.

2. The method according to claim 1, wherein the at least one fucosylated oligosaccharide further comprises an additional fucosylated oligosaccharide selected from the group consisting of 3'fucosyllactose, difucosyllactose, lacto-N-fucopentaose I, lacto-N-fucopentaose II, lacto-N-fucopentaose III, lacto-N-fucopentaose V, lacto-N-fucohexaose, lacto-N-difucohexaose I, fucosyllacto-N-hexaose, fucosyllacto-N-neohexaose I, fucosyllacto-N-neohexaose II, difucosyllacto-N-hexaose I, difucosyllacto-N-neohexaose I, difucosyllacto-N-neohexaose II, fucosyl-para-Lacto-N-hexaose, and combinations thereof.

3. The method according to claim 1, wherein the at least one fucosylated oligosaccharide comprises a 2' fucosyl-epitope.

4. The method according to claim 1, wherein the 2'FL is the only fucosylated oligosaccharide in the nutritional composition.

5. The method according to claim 1, wherein the at least one N-acetylated oligosaccharide further comprises lacto-N-tetraose (LNT).

6. The method according to claim 1, wherein the at least one N-acetylated oligosaccharide further comprises para-lacto-N-neohexaose (para-LNnH).

7. The method according to claim 1, wherein a weight ratio of the at least one fucosylated oligosaccharide to the at least one N-acetylated oligosaccharide is from 1:10 to 12:1.

8. The method according to claim 1, wherein the nutritional composition comprises at least another oligosaccharide and/or fiber and/or a precursor of a human milk oligosaccharide selected from the group consisting of fructo-oligosaccharides (FOS), xylooligosaccharides (XOS), inulin, polydextrose, sialylated oligosaccharides, N-acetylated oligosaccharides, sialic acid, fucose and combinations thereof.

9. The method according to claim 1, wherein the composition does not comprise any sialylated oligosaccharide.

10. The method according to claim 1, wherein the nutritional composition comprises at least one probiotic in an amount of from $10^3$ to $10^{12}$ cfu/g dry weight of the nutritional composition.

11. The method according to claim 1, wherein the nutritional composition is in a form selected from the group consisting of an infant formula, a starter infant formula, a follow-on or follow-up infant formula, a baby food, an infant cereal composition, a fortifier and a supplement.

12. The method according to claim 1, wherein the infant or young child is at risk of developing an allergy selected from the group consisting of: allergic sensitization, food allergy, atopic dermatitis and eczema, wheezing, asthma, allergic rhinitis, rhino-conjunctivitis, eosinophilic esophagitis, hypersensitivity, anaphylaxis, urticaria, angioedema food intolerance, and allergy deriving from allergenic proteins in food, pollen, animal dander, house dust mite, or venom.

13. The method according to claim 1, wherein the 2'FL and the LNnT are the only human milk oligosaccharides in the nutritional composition.

* * * * *